United States Patent [19]
Fletcher

[11] 4,281,897
[45] Aug. 4, 1981

[54] PHOTOMETRIC SYSTEM INCLUDING A TIME-DIVISION OPTICAL ATTENUATOR

[76] Inventor: Taylor C. Fletcher, 1534 Sunny Crest Dr., Fullerton, Calif. 92635

[21] Appl. No.: 2,398

[22] Filed: Jan. 10, 1979

[51] Int. Cl.³ ............................................. G05D 25/00
[52] U.S. Cl. .................... 350/274; 250/233; 356/434
[58] Field of Search ................ 356/433, 434, 435; 250/233; 350/266, 269, 273, 274, 314, 272

[56] References Cited

U.S. PATENT DOCUMENTS

| | | | |
|---|---|---|---|
| 2,678,581 | 5/1954 | Reisner | 356/434 |
| 3,303,271 | 2/1967 | Hecker | 350/272 |
| 3,435,213 | 3/1969 | Colbow et al. | 250/233 |
| 3,560,098 | 2/1971 | Witte et al. | 356/434 |

*Primary Examiner*—R. A. Rosenberger
*Attorney, Agent, or Firm*—Keith D. Beecher

[57] ABSTRACT

A photometric system is provided for use as a spectrophotometer system; or for use as a calibration system for accurately calibrating optical attenuators, such as neutral glass filters, interference-type filters, comb filters, screen filters, and the like. The photometric system of the invention includes a time-division optical attenuator which causes the precise fraction of a light beam to be passed through the system. The time-division optical attenuator is adjustable, so that when an optical attenuator to be calibrated, or a sample to be tested, is introduced into the optical path of the system, the light incident thereon can be changed precisely by any ratio of integers which returns the light output of the system to nearly its original reference level. Since the optical time-division attenuator can make changes in light intensity which are theoretically without error, the accuracy of the system depends only upon the accuracy by which the small difference between the output light from the system under test conditions and the output light from the system under reference conditions can be measured.

27 Claims, 11 Drawing Figures

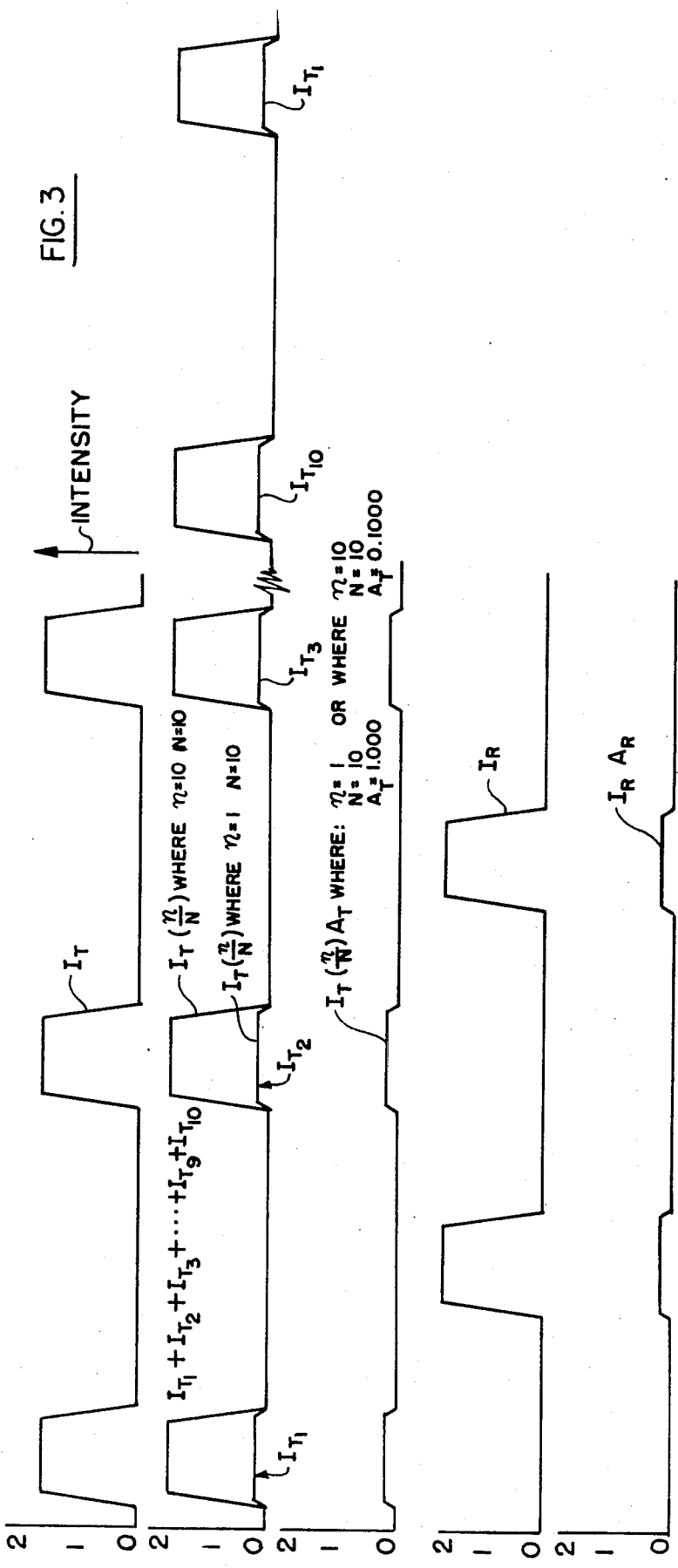
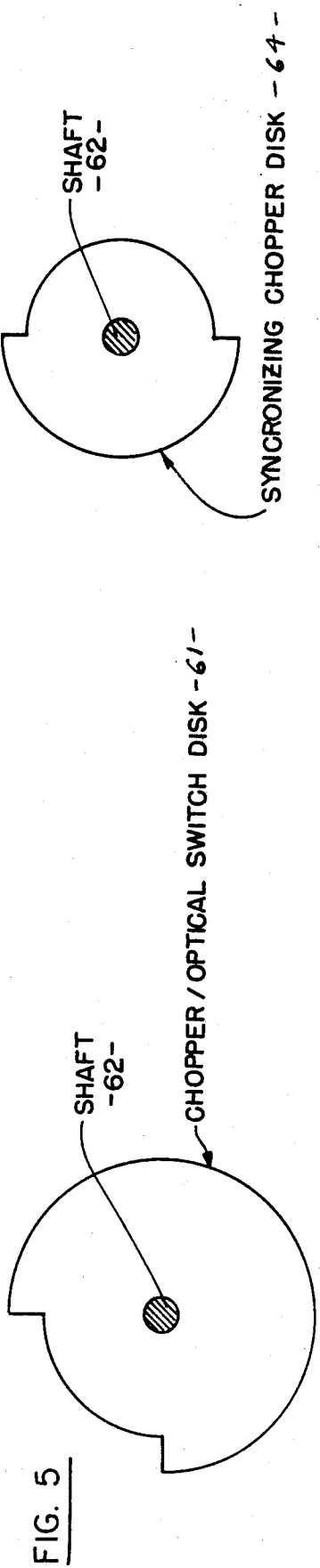

SHUTTER AND MASK OF TIME DIVISION ATTENUATOR (CONFIGURED FOR N=10)

FILTER HOLDER AND FILTERS UNDER TEST

PHOTOMETRIC SYSTEM INCLUDING A TIME-DIVISION OPTICAL ATTENUATOR

BACKGROUND

As mentioned above, the photometric system of the invention can be used for spectrophotometric purposes, or for calibrating optical attenuators. The use of optical attenuators of known attenuation in spectrophotometric systems, and the like, requires that the attenuation of such attenuators be known to a precise degree. However, the calibrated accuracy of optical attenuators, such as neutral density glass filters, interference-type filters, comb filters, screen filters, and the like, has been limited in the prior art, especially at high optical densities. Accordingly, there is a pressing need to provide greater accuracy in the measurement of the attenuation of such attenuators, and one purpose of the system of the present invention is to provide a means for fulfilling that need.

Accordingly, one objective of the present invention is to provide a photometric system for precisely calibrating optical attenuators, and the like; and another objective of the invention is to provide such a photometric system which may be used for spectrophotometric purposes.

The photometric system of the invention, as mentioned above, includes a time-division optical attenuator which is used to attenuate a light beam within the system with a high degree of accuracy. The photometric system of the invention is such that non-linearities are eliminated, so that the transmittance (T) of a sample, or the calibration of an optical attenuator, may be achieved with a high degree of accuracy.

The photometric system of the invention, when used to calibrate an optical attenuator, for example, first measures the light passing through a reference attenuator. The optical attenuator to be calibrated is then introduced into the system, and the light incident on the latter attenuator is changed precisely by any ratio of integers by the time-division attenuator included in the system, so as to return the light output of the system to nearly its original reference level. As mentioned above, since the time-division optical attenuator can make changes in the light intensity which are theoretically without error, the accuracy of the measurement of the attenuator being calibrated depends only on the accuracy to which the small difference between the reference and test light outputs of the system can be measured.

For example, if an attenuator to be calibrated passes 9.8% of the incident light, the optical division attenuator is changed from the reference to the test mode of the system to pass exactly ten times the amount of light, so that the accuracy of the calibration will depend upon how accurately one can measure the 2% change in the output light signal levels between the reference and the test conditions.

BRIEF DESCRIPTION OF THE DRAWINGS

FIG. 3 is a series of curves showing the time relationship between the light signals passing through various sections of the system of FIGS. 1 and 2;

FIG. 5 is a plan view of a chopper/optical switching disc associated with an optical switch and chopper included in the system of FIGS. 1 and 2;

FIG. 6 is a plan view of a synchronizing chopper disc which is included in the system of FIGS. 1 and 2;

DETAILED DESCRIPTION OF THE ILLUSTRATED EMBODIMENTS

Figure 1:
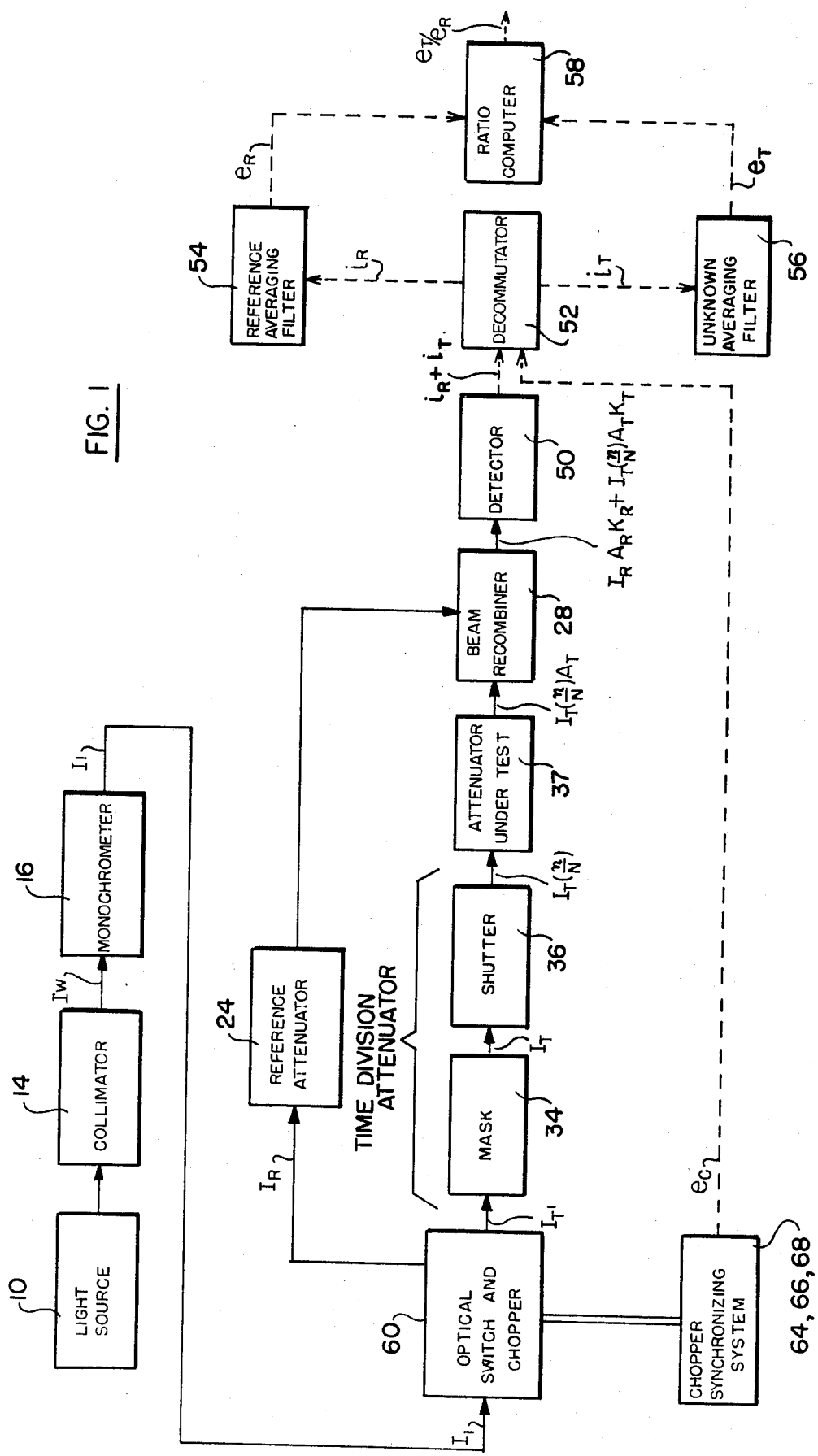
FIG. 1 is a block diagram of a photometric system representing a presently preferred embodiment of the invention, and which is used for calibrating an optical attenuator.

The photometric system of FIG. 1 is used to calibrate a neutral density glass filter, represented as the "attenuator under test 37". Such glass filters can be made to be uniform over their surface, and the system of FIG. 1 enables one to calibrate and measure precisely the attenuation of such a filter. The same system can be used to measure precisely the attenuation of other devices, such as, for example, a comb attenuator, a screen attenuator, or the like. The attenuation of such devices may be measured at any selected wavelength, band of wavelength, or group of wavelengths.

The photometric system of FIG. 1 includes a light source 10 which generates a white light beam at a mean wavelength ($\lambda_W$). The light beam from source 10 is passed through a collimator 14, and a collimated white light beam ($I_W$) from the collimator is passed through a monochrometer 16. The monochrometer produces a narrow bandwidth unmodulated monochromatic light beam ($I_1$) at a mean wavelength ($\lambda_1$).

The unmodulated monochromatic light beam ($I_1$) from monochrometer 16 is then passed through a combination optical switch and chopper 60 which converts the unmodulated light beam ($I_1$) into two separate pulsating light beams ($I_R$) and ($I'_T$) both at wavelength ($\lambda_1$); the pulsating light beams constituting respectively the reference beam and the test beam.

As shown in FIG. 3, the light pulses forming the light beams ($I_R$) and ($I'_T$) alternate in time, and they are separated from one another in time by a dark period during which no light passes through the system. The reference beam ($I_R$) provides a reference to correct for system variations, such as source intensity changes and detector sensitivity changes.

The reference beam ($I_R$) from the optical switch and chopper 60 is directed through the reference channel of the system, and is passed through a reference attenuator 24. Reference attenuator 24 serves to maintain a reasonable signal balance between the reference and test beam outputs. The attenuated light beam ($I_R A_R$) from the reference attenuator is introduced to a beam recombiner 28, where a fixed fraction ($K_R$) of the attenuated reference beam ($I_R A_R$) is combined with the test beam output. The output of the recombiner 28 is directed to a photodetector 50 which may, for example, be a photomultiplier tube.

Figure 4:
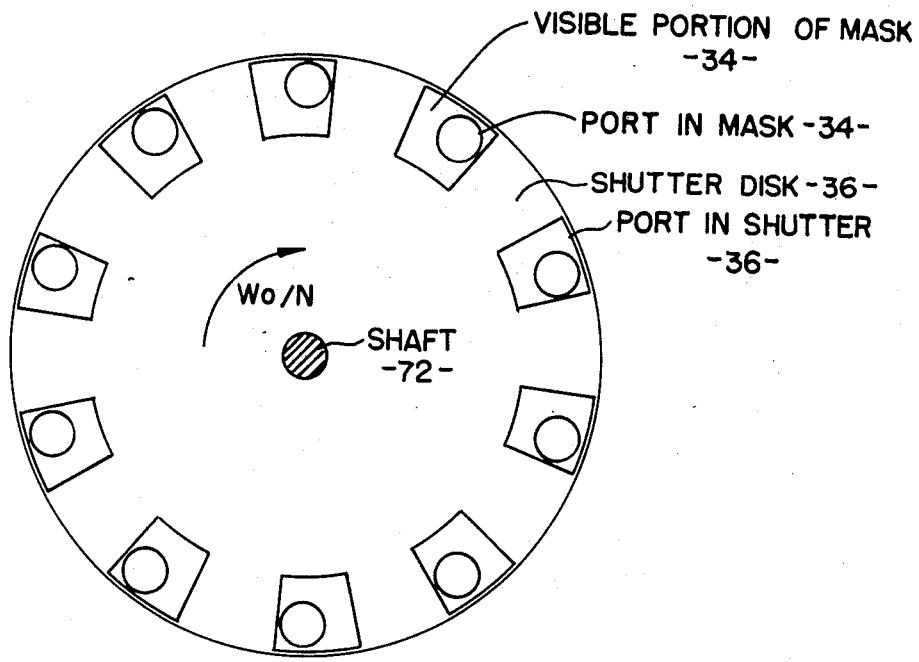
FIG. 4 is a plan view of a mask and shutter associated with a time-division attenuator which is included in the systems of FIGS. 1 and 2.
Figure 7:
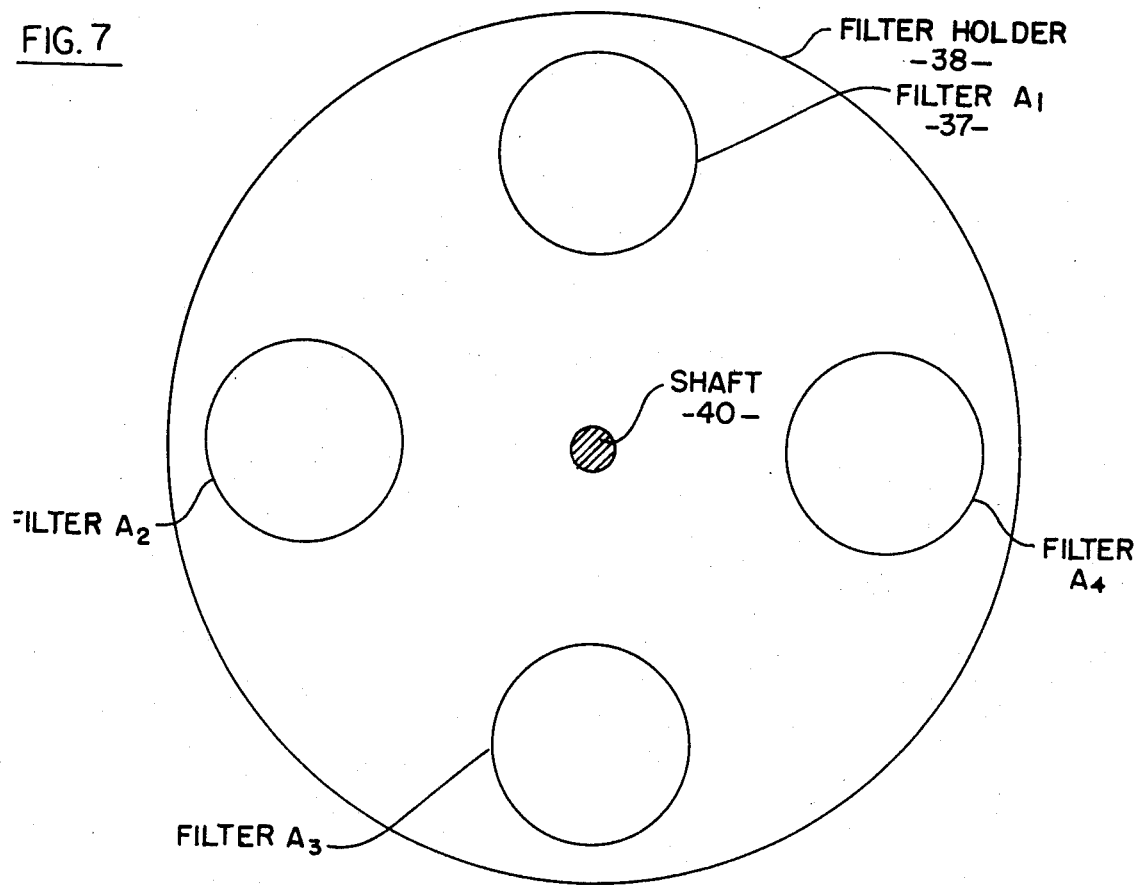
FIG. 7 is a plan view of a filter holder and filters to be calibrated in the system of FIGS. 1 and 2.

The test light beam ($I'_T$) of wavelength ($\lambda_1$) from optical switch and chopper 60 is directed through the test channel of the system, and is passed through a time-division attenuator consisting of a stationary mask 34 and a rotating shutter 36, shown in some detail in FIG. 4. A fixed portion ($I_T$) of the beam ($I'_T$) passes through ports in the mask 34. Typically, mask 34 and shutter 36 have the same number (N) of ports. Any number (n) of the ports of shutter 36 are open for any particular test, and the remaining ports are closed. Therefore, for that particular test, the output of the shutter is a beam of intensity (($n/N)I_T$).

It should be stressed that all the pulsating light beam $I_T$ is directed to the stationary mask 34, and that the only function of the mask is to form the pulsating light beam $I_T$ into N parallel pulsating light beams $I_T$. There are thus N pulses of an average value p leaving mask 34 for every pulse $p_T$.

Now shutter 36 has N ports each of which ports may be arbitrarily and independently opened or closed. Thus any number of ports from 1 to N may be open.

The ports in the shutter 36 are so designed and the shutter 36 so synchronized with the light pulses such that an open port in the shutter 36 will never even partially attenuate a light pulse p, which has passed through a port in mask 34. That is, each light pulse P is either passed through the shutter 36, or completely blocked by the shutter.

It can be seen that if n ports are open in shutter 36 and there are N ports in mask 34 and N ports in shutter 36 (only n of which are open) that only n/N pulses of average value p pass through the shutter 36 for each pulse $p_T$. As the shutter rotates it sequentially passes through a specific shutter port the light pulses $p_1$, then $p_2$ then $p_3$ - - - $p_{N-1}$ then $p_n$.

For example if only shutter ports 1 and 2 are open and all others closed, then after one complete revolution of the shutter 36 (N pulses of $P_T$) the following pulses will have passed through shutter 36:

total light = $(p_1+p_2)+(p_2+p_3)=(p_3+p_4)= \cdots$
$+(P_{N-2}+P_{N-1})+(p_{N-1}+p_N)+(p_N+p_1)=2Np$ while if all the ports in shutter 36 are open then after one complete revolution of shutter 36 (N pulses of $P_T$) the following pulses will have passed through shutter 36 total light = $Np_1+Np_2+Np_3+ \cdots$
$Np_{N-1}+N_p=N^2p$

Therefore it can be seen that the ratio of total light passed through shutter 36 for the case where only 2 shutter ports are open and the case where all shutter ports are open is exactly 2/N. This technique results in an absolutely accurate method of producing the ratio of two light beams.

As shown in FIG. 4, the ports of shutter 36 are larger than the ports of mask 34. The shutter ports are so positioned and synchronized with respect to the light pulses of beam ($I_T$) passing through the ports of mask 34 than an open shutter port never partially obstructs a light pulse of beam ($I_T$). The shutter 36 is rotated on shaft 72 (FIG. 2) in synchronism with the optical swiitch and chopper 10, advancing one shutter port for each light pulse of beam ($I_T$). Therefore, at the end of every N pulses of beam ($I_T$) from mask 34, exactly n pulses of the beam will be passed through every open port of shutter 36, the value of n being dependent upon the number of shutter ports which are open. Thus, by changing the number of open ports of shutter 36 it is possible very precisely to adjust the average amount of light passing through the shutter. The ratio of the average light intensity from one setting of the shutter ($n_1$) to the next setting of the shutter ($n_2$) is exactly the ratio of two integers. It should be noted that the pulses of light passing through any one port of mask 34 are equal in amplitude, repetition rate and duration.

During any one complete revolution of shutter 36 exactly N pulses of light will pass through each port of mask 34, however, only n of these N pulses of light will find an open port in the shutter, and the other (N−n) pulses will be blocked by the shutter. Furthermore, during each revolution of the shutter, N pulses of light will pass through each open shutter port.

By using collimated light of uniform intensity; by making the ports of mask 34 symmetrical about the optical axis; by making the ports of the mask of precisely the same size, the effects of non-linearities and off-sets in detector 50 and in the electronics associated with the detector are further reduced.

The test light beam ($I_T(n/N)$) leaving the shutter 36 is then passed through the optical attenuator 37 under test which has an attenuation factor ($A_T$). If the attenuator 37 under test has uniform attenuation over its surface, then the ports of the shutter are preferably circular for ease in making them precise. However, if the attenuator under test does not have uniform attenuation over its surface, it is then necessary to use pie-shaped ports. Moreover, the attenuator under test may be rotated slowly about its optical axis while it is being calibrated so that all active portions of its surface will be exposed equally to the light beam.

The test light beam ($I_T(n/N)A_T$) then passes through the beam recombiner 28 where a fixed portion ($K_T$) of the test light beam is combined with a fixed portion ($K_R$) of the reference light beam ($I_R A_R$). The resultant interleaved series of pulses form a light beam ($I_R A_R K_R + I_T(n/N)A_T K_T$) which is directed to the photodetector 50. The electric output current ($i_R + i_T$) from the detector passes into decommutator 52 which separates the electric current pulses ($i_R$ and $i_T$). The pulses ($i_R$ and $i_T$) are respectively introduced into averaging electronics filters 54 and 56 which respectively provide unmodulated output voltages ($e_R$ and $e_T$). The output ($e_T$) of test current filter 56 is divided by the output ($e_R$) of reference current filter 54 in the ratio computer 58 which calculates ($e_T/e_R$).

For any one set of tests, only the value ($A_T$) of the attenuator under test 37, and the number of open ports (n) in the shutter 36 are changed. Therefore, if there are two tests labelled Test 1 and Test 2, then if $n_1$ and $n_2$ are selected so that:

$n_1 A_{T1} = n_2 A_{T2}$ the ratio of the two attenuators $A_{T1}$ and $A_{T2}$ is given by $A_{T1}/A_{T2} = n_2/n_1$.

Figure 2:
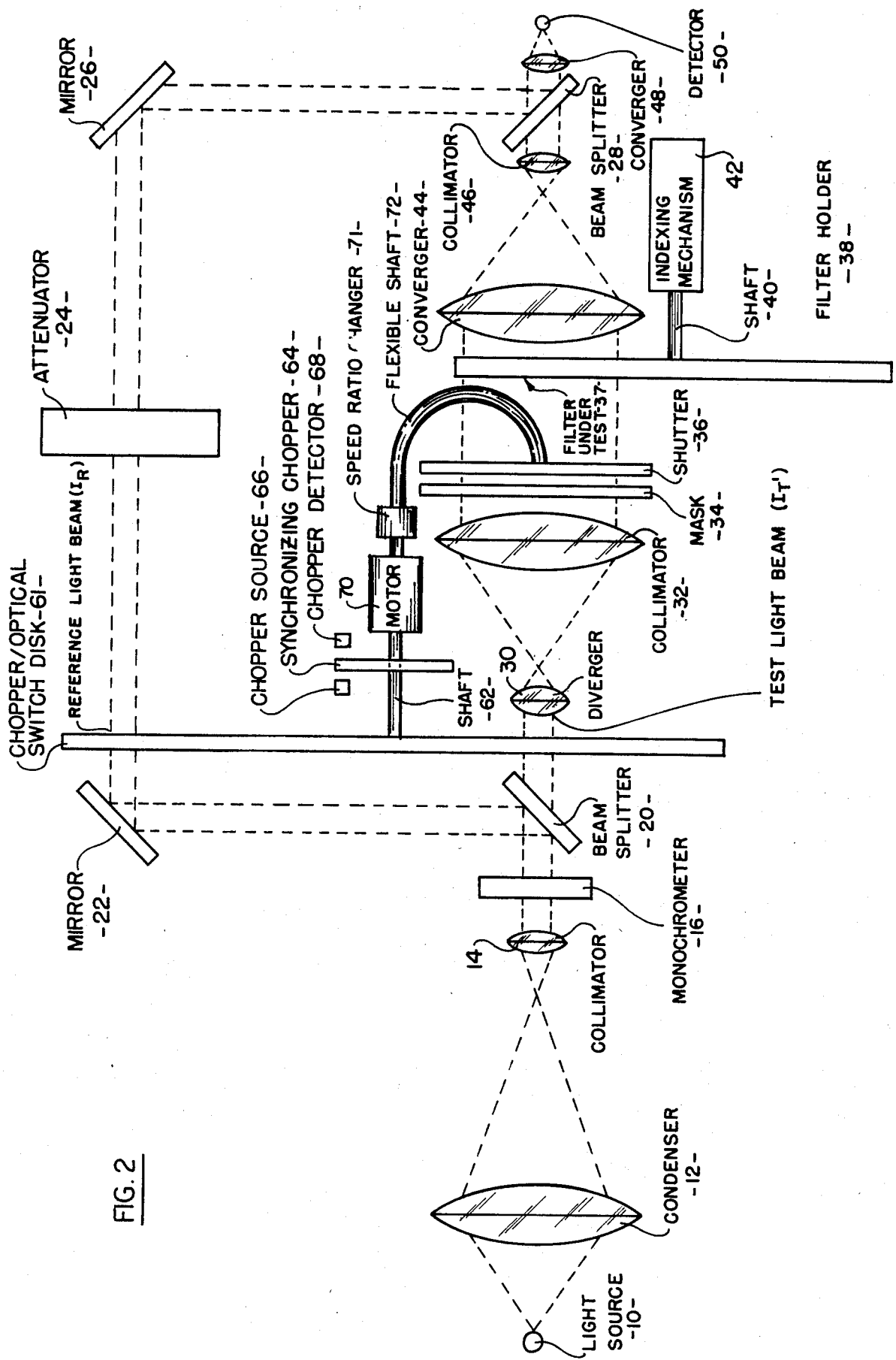
FIG. 2 is a schematic representation of the optical elements used in the photometric system of FIG. 1.

For example, in the system of FIGS. 1 and 2 for calibrating optical attenuators such as neutral density filters, a filter holder 38 holds several neutral density filters which may be compared with one another. Such filters can be used as a set, and the system of FIGS. 1 and 2 supplies accurate information as to their relative attenuation values. Similarly, if one of the filters is completely removed from the filter holder 38, the ratio measured by the system is with respect to the fluid which fills the photometric system, which usually is air, although other fluids, or a vacuum, may be used.

In FIG. 2, which is a schematic representation of the optical components used in the system of FIG. 1, light from source 10 passes through a condensing lens 12, collimator lens 14, a monochrometer 16 (such as a narrow bandwidth interference filter), and then into the combination chopper/optical switch 60. The combination chopper/optical switch 60 consists of a beam splitter 20, a mirror 22, a chopper/switch disc 61 and a motor 70.

The monochromatic, collimated light beam ($I_1$) is divided by beam splitter 20 into two unmodulated light beams. A motor 70 turns shaft 62, on which are mounted the optical switch and chopper disc 61 and a synchronizing chopper disc 64. The unmodulated light beams are chopped, alternately forming light beams ($I_R$) and ($I'_T$). The first unmodulated light beam, after being reflected by beam splitter 20, is reflected by mirror 22, and is alternately blocked and passed by chopper/switch disc 61 converting it into the modulated light beam ($I_R$). The modulated light beam ($I_R$) then passes through attenuator 24, is reflected by mirror 26, is partially reflected by beam splitter 28, and is directed to converging lens 48 which focuses the beam onto the detector 50.

Similarly, the second unmodulated light beam passing through beam splitter 20 is modulated by the chopper 61 to form the modulated test light beam ($I'_T$). Light beam ($I'_T$) consists of a series of light pulses which alternate in time with the light pulses of the reference light beam ($I_R$), and which are all separated in time by dark periods in which both ($I'_T$) and ($I_R$) are dark, as shown in FIG. 3. The test beam ($I'_T$) is increased in size and collimated evenly to deliminate the filter under test, this being accomplished by diverging lens 30 and collimator 32, as shown in FIG. 2.

The shutter 36, as shown in FIG. 2, is driven by a motor 70 through a speed ratio changer 71 and a flexible shaft 72. The speed ratio changer 71 reduces the speed of flexible shaft 72 and shutter 36 to 1/N the speed of motor 70. The chopper/optical switch generates one pulse of light for the test beam ($I_T$) for each revolution of motor 70, thus the shutter will advance one port for every light pulse of beam ($I_T$). The light beam ($I_T$), after passing through the shutter passes through the attenuator under test 37, the latter attenuator being mounted in an attenuator holder 38. The light beam ($I_T$) is then reduced to size and recollimated by a converging lens 44 and collimating lens 46, as shown in FIG. 2. A fixed portion of the test light beam ($I_T$) is then combined with a fixed portion of the reference light beam ($I_R$) in recombiner 28, which may take the form of a beam splitter. The resultant light beam ($I_R + I_T$) is directed to the photodetector 50 by converging lens 48.

A light source 66 is provided for chopper 64, this light source typically taking the form of a light emitting diode. The light source provides a light beam which is modulated into a square wave by the synchronizing chopper 64. The modulated light beam is detected by a photodetector 68, which may, for example, be a phototransistor. The output of the detector 68 is a synchronous electric signal ($e_C$) which provides the decommutator 52 (FIG. 1) with the information it needs to separate the electric current pulse ($i_T$) and ($i_R$) and to direct these pulses to their respective electronic filters 56 and 54.

The following is an example which uses the calibration system of FIGS. 1 and 2 to determine the relative attenuation of two precision neutral density filters. All measurements are taken at a narrow light band centered at some wavelength ($\lambda_1$). Filter A is designed to have 90% T (an optical density of 0.0458), and filter B is designated to have 9% T (an optical density of 1.0458). Thus, only 10% as much light passes through filter B as passes through filter A, and the relative optical density of the two filters is 1.000 absorbance units. The shutter and mask 36, 34 each has ten ports, with all mask ports being open for all measurements. When the attenuation of filter A is being measured only one port of shutter 36 is open; and when the attenuation of filter B is being measured, all of the shutter ports are open. Thus, precisely ten times as much light reaches filter B during each series of ten light pulses reaching filter A, during each series of ten light pulses passing through mask 34. The ratio of the two outputs from computer 58, namely, $$\frac{\text{Output } B}{\text{Output } A} = \frac{e_{TB}/e_{rB}}{e_{TA}/e_{RA}}$$

is a measure of the deviation of the desired 10:1 ratio of transmittance of filter A/filter B.

For example, if the average output signal,

Output BA = Output B/Output A = 1.0252 then the transmittance of Filter B is 10.252% that of Filter A. (A relative optical density of 0.9892 absorbance units). As the signals are nearly identical to all times, very precise comparisons can be made.

Similarly, for a pair of filters A' and B' with a transmittance ratio of 3:1, the same ten port system can be used with three ports open in the shutter 36 when filter A' is inserted and nine ports open when filter B' is inserted.

To calibrate a filter C which has a transmittance of approximately 0.9% T, filter B can be substituted for filter A in the first example and filter C for filter B. If the ratio of Output CB = Output C/Output B = 0.9950 then the attenuation ratio of filter C with respect to filter A is given by, $$\text{Relative Attenuation}_{CA} = \frac{A_{BA} A_{CB}}{(\text{Output } BA)(\text{Output } CB)}$$

$$= \frac{(10/1)(10/1)}{(1.0252)(0.9950)}$$

$$= 98.0321 : 1$$

Where:

$A_{BA}$ = Time division attenuator ratio change between test B and test A.

$A_{CB}$ = Time division attenuation ratio change between test C and test B.

If test A had been taken with no filter and in an air environment, and all the test results were the same as above then: The absolute attenuation of filter C with respect to air (including reflection losses) would be 98.0321:1. Filter C would have an apparent optical density of 1.9914 absorbance units.

FIG. 3 shows the phase relationship between the test beam ($I_T$) and the reference beam ($I_R$). In the example there are 10 parallel beams of light which make up ($I_T$). When n equals 10, then all of the light beams pass through the shutter with every light pulse, while if n=1, then only one beam will pass through the shutter with every light pulse. This is expressed algebraically by the following equations.

$$[I_{T(n/N)}]_{n=10} = I_{T1} + I_{T2} + I_{T3} + I_{T4} + I_{T5} + I_{T6} + I_{T7} + I_{T8} + I_{T9} + I_{T10}$$

While of n=1

$$[I_{T(n/N)}]_{n=1} = I_{T1} \text{ or } I_{T2} \text{ or } I_{T3} \text{ or } I_{T4} \text{ or } I_{T5} \text{ or } I_{T6} \text{ or } I_{T7} \text{ or } I_{T8} \text{ or } I_{T9} \text{ or } I_{T10}$$

The precision of the system is shown by the following two equations. These equations show the total energy which has passed through the system in ten light pulses.

$$[I_{T(n/N)}]_{n=10} = 10(I_{T1} + I_{T2} + I_{T3} + I_{T4} + I_{T5} + I_{T6} + I_{T7} + I_{T8} + I_{T9} + I_{T10})$$

$$[I_{T(n/N)}]_{n=1} = I_{T1} + I_{T2} + I_{T3} + I_{T4} + I_{T5} + I_{T6} + I_{T7} + I_{T8} + I_{T9} + I_{T10}$$

Note that the ratio is exactly 10:1.

It is to be understood that the reference and test channels may be interchanged, and the system operated to match attenuations in the two channels, rather than holding one channel constant.

Figure 8:
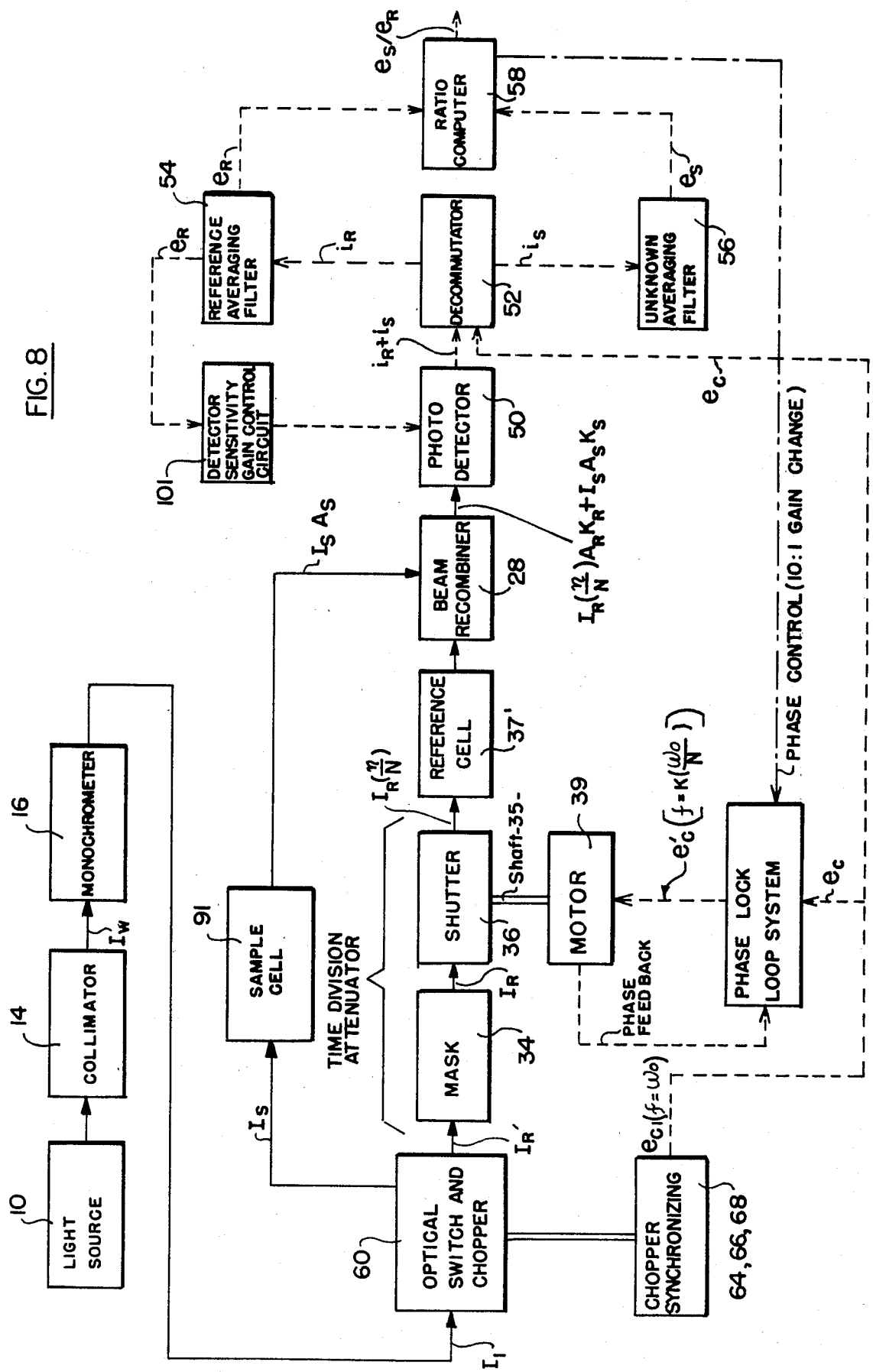
FIG. 8 is a block diagram of a scanning spectrophotometer which uses a time-division attenuator in accordance with the concepts of another embodiment of the invention precisely to attenuate the reference beam of a dual beam spectrophotometer.
Figure 9:
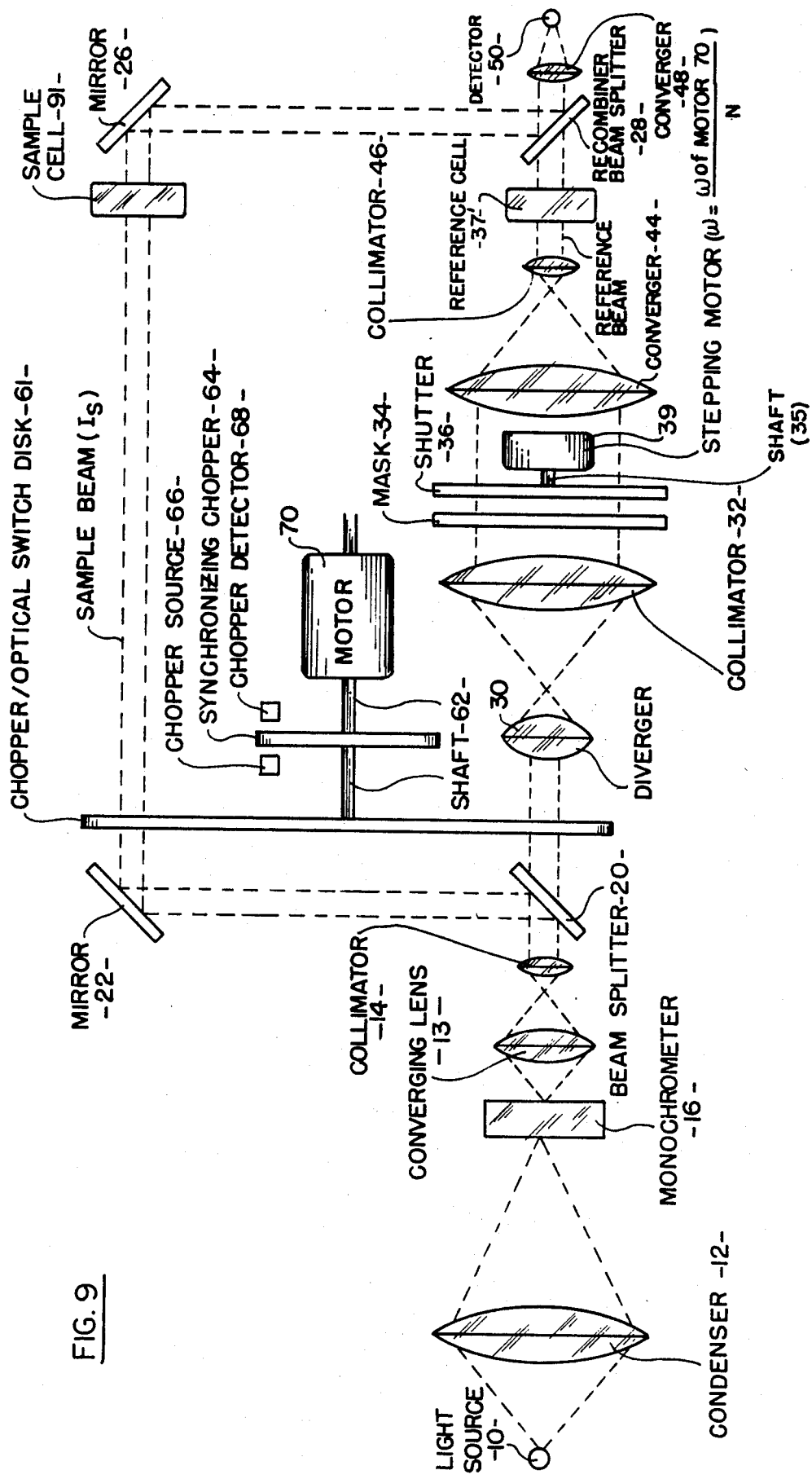
FIG. 9 is a schematic representation of the optical elements of the system of FIG. 8.

In the photometric system of FIGS. 8 and 9, the timedivision attenuator is used in a dual beam spectrophotometric system to increase the dynamic range of the system while maintaining a high degree of accuracy. In accordance with the invention, the overall system gain is automatically changed to maintain a constant detector output for the reference channel. This enables the system to operate at the most efficient operating point.

Specifically, the time division attenuator is used in the system of FIGS. 8 and 9 for accurately attenuating the intensity of the reference beam to reference cell 37', which replaces the attenuator under test 37 in the system of FIGS. 1 and 2. The test or sample beam ($I_S$) in the spectrophotometric system of FIGS. 8 and 9, is passed through a sample cell designated 91. The other components of the system of FIGS. 8 and 9 are similar to the components of the system of FIGS. 1 and 2, and have been designated by the same reference numerals.

By making the monochrometer 16 wavelength adjustable, for example, by using a rotating prism; and, as shown in FIGS. 8 and 9, by inserting the reference cell 37' between collimator 46 and beam recombiner 28, and by inserting the sample cell 91 between the optical switch and chopper 60 and beam recombiner 28, the calibration system of FIGS. 1 and 2 is converted into a dual beam spectrophotometer which has the capability of very accurate scale expansion, by using the techniques described above. In the latter embodiment, the shutter 36 is driven by a stepping motor 39 which is synchronized by a phase locked loop system 51 under the control of the ratio computer 58, as shown in FIG. 8.

In the system of FIG. 8, the output of the photodetector 50 is synchronously demodulated so that two outputs are obtained, one for the reference channel ($e_R$) and one for the sample channel ($e_S$). Both the reference cell 37' and sample cell 91 contain a solvent which has varying absorptivity over the wavelengths of interest. The intensity of the source and the sensitivity of the photodetector also vary with wavelength. The sample cell also contains a small amount of unknown material whose absorption varies between 2% and 99.8%.

The spectrophotometric system includes a minor feedback loop which feeds the output ($e_R$) of the reference averaging filter 54 into the detector sensitivity gain control 101, which, in this example, is the power supply for the photomultiplier detector 50. This servo loop consists of detector 50, decommutator 52, reference averaging filter 54 and the detector sensitivity gain control circuit 101. As the reference light beam ($I_R$) is reduced in intensity, or the cathode sensitivity of the photodetector 50 decreases, the voltages applied to the photomultiplier tube dynodes of the detector are increased sufficiently to maintain the reference voltage ($e_R$) nearly fixed. This enables the system to function in an optimum condition as far as linearity and system noise is concerned.

In the example, the output ratio $e_S/e_R$ will vary from 0.998 to 0.002 (99.8 to 0.2%T). With the incorporation of an optical attenuator in series with the reference light path, it is possible to decrease the reference light beam when the unknown material in the sample reaches some predetermined level of absorption. In the example, assume that the predetermined switch over is 10% (with some hysteresis if chart recording is used). If the reference light beam is then attenuated by a factor of 10:1, the detector sensitivity will automatically be increased by 10:1. This makes the signal out of the spectrophotometer much more accurate than previously whenever $e_S/e_R$ is less than 0.1.

In the system of FIGS. 8 and 9, light from source 10, (which may be for instance an incandescent lamp) is gathered and focused by condensor lens 12 on the entrance slit of monochrometer 16. The monochrometer may consist of an entrance slit, a collimating mirror, a quartz prism and an output mirror which focuses monochromatic light on the output slit. Lens 13 gathers the light from the exit slit and collimator 14 converts it into a compact collimated monochromatic light beam.

Figure 10:
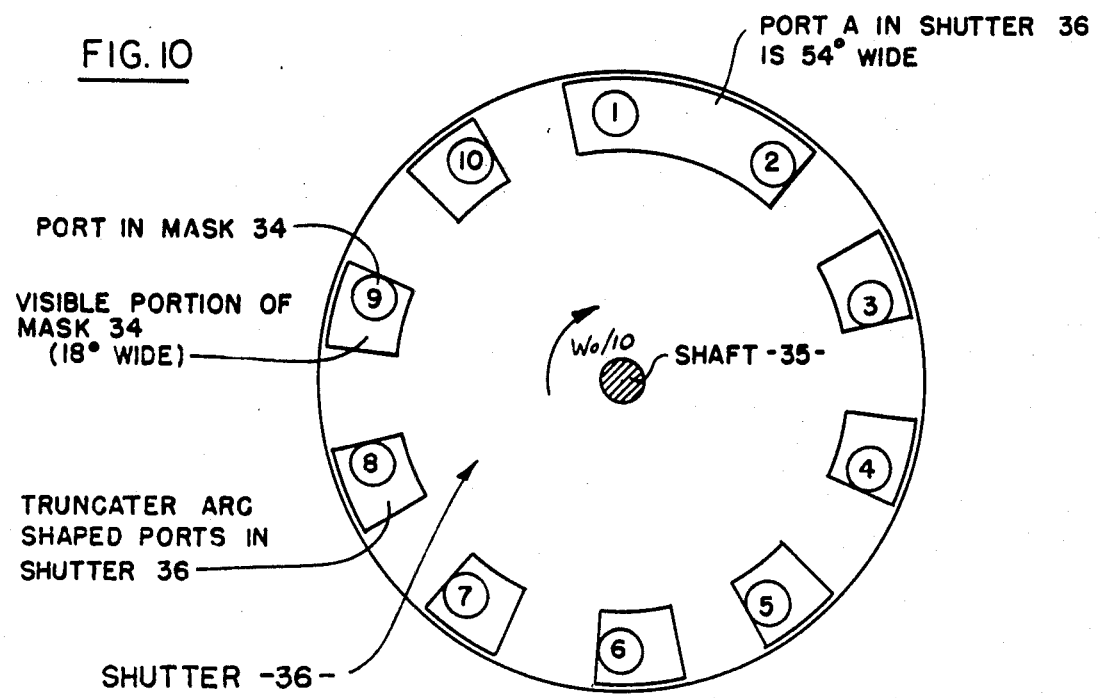
FIG. 10 is a representation of a shutter and mask for use in the system of FIGS. 8 and 9.

The monochromatic light beam is separated by beam splitter 20 into a reference light beam and a sample light beam. The reference beam passes directly through the beam splitter 20 and is chopped by chopper/optical switch disc 61. This chopped reference beam ($I'_R$) is enlarged by diverger lens 30 and recollimated by collimator lens 32. The collimated and chopped light beam ($I'_R$) passes through mask 34 where it now has a value of ($I_R$). Depending on the relative phase of stepping motor 35 with respect to optical disc 61, the light beam ($I_R$) will either be passed by shutter 36 with absolutely no attenuation or with exactly an average attenuation of 10:1. FIG. 10 details a shutter/mask combination which by shifting the shutter (36) 18° with respect to the light pulses will accomplish this 10:1 shift in attenuation. The reference light beam will then be either ($I_R$) or ($I_R/10$). This reference light beam is converged by lens 44 and recollimated by collimator 46. The light beam then passes through the reference cell 37' and is combined (actually interlaced) with the sample beam by beam splitter recombiner 28. The resultant light beam is focused by converging lens 48 upon detector 50.

Similarly, the sample light beam portion of the monochromatic light beam impinging upon beam splitter 20 is reflected by mirror 22, is chopped by chopper/optical switch disc 61 to form a pulsating monochromatic light beam ($I_S$) which is interlaced in time with pulsating light beam ($I_R$). It should be noted that the phase relationship of FIG. 3 applies if ($I_S$) of FIG. 8 is substituted for ($I_R$) of FIG. 3, and ($I_R$) of FIG. 8 is substituted for ($I_T$) of FIG. 3.

The pulsating light beam ($I_S$) passes through sample cell 91, is reflected by mirror 26, and combined (interlaced) with the reference light beam ($I_R$) by beam splitter 28. The combined light beam is focused by lens 48 upon detector 50. The output of the detector 50 (if it is a photomultiplier tube) is a series of current pulses alternately of value ($i_R$) and ($i_S$) which correspond to the signals generated in the detector by respectively the reference and sample light beams. ($i_R$) and ($i_S$) along with the chopper synchronizing signal are fed into decommutator 52 which separates the detector output into two individual electrical outputs ($i_R$) and ($i_S$).

The reference averaging filter 54 converts the ($I_R$) signal to a non-pulsating voltage ($e_R$) which is proportioned to $I_R(n/N)A_R K_R$. ($e_R$) is fed into the detector sensitivity gain control circuit 101, where it is compared with a fixed reference voltage ($E_R$). If ($e_R$) is larger than ($E_R$) the gain of the detector is decreased until ($e_R$) equals ($E_R$). If the detector is a photomultiplier tube, the detector sensitivity gain control circuit supplies the dynode voltages for the photomultiplier tube. If the gain of the photomultiplier needs to be increased, the magnitude of the voltages applied to the dynodes are increased and the voltages are decreased if the gain needs to be decreased.

The ($i_S$) signal from decommutator 52 passes into the unknown averaging filter 56 and the output is a voltage ($e_S$) which is a non-pulsating signal proportional to $I_S A_S$. ($e_S$) and ($e_R$) are then fed into the ratio computer and a ratio $e_S/e_R$ is generated. When $e_S/e_R$ becomes less than 0.08 the computer generates a phase control signal which shift the relative phase of shutter 36 with respect to optical switch and chopper 60. The ratio computer 58 has memory which remembers that it has switched the reference attenuator thus increasing the value of $e_S/e_R$ by a factor of 10. When $e_S/e_R$ reaches 1.00, the phase control is switched back to its original condition and $e_S/e_R$ is no longer expanded by a factor of 10.

Figure 11:
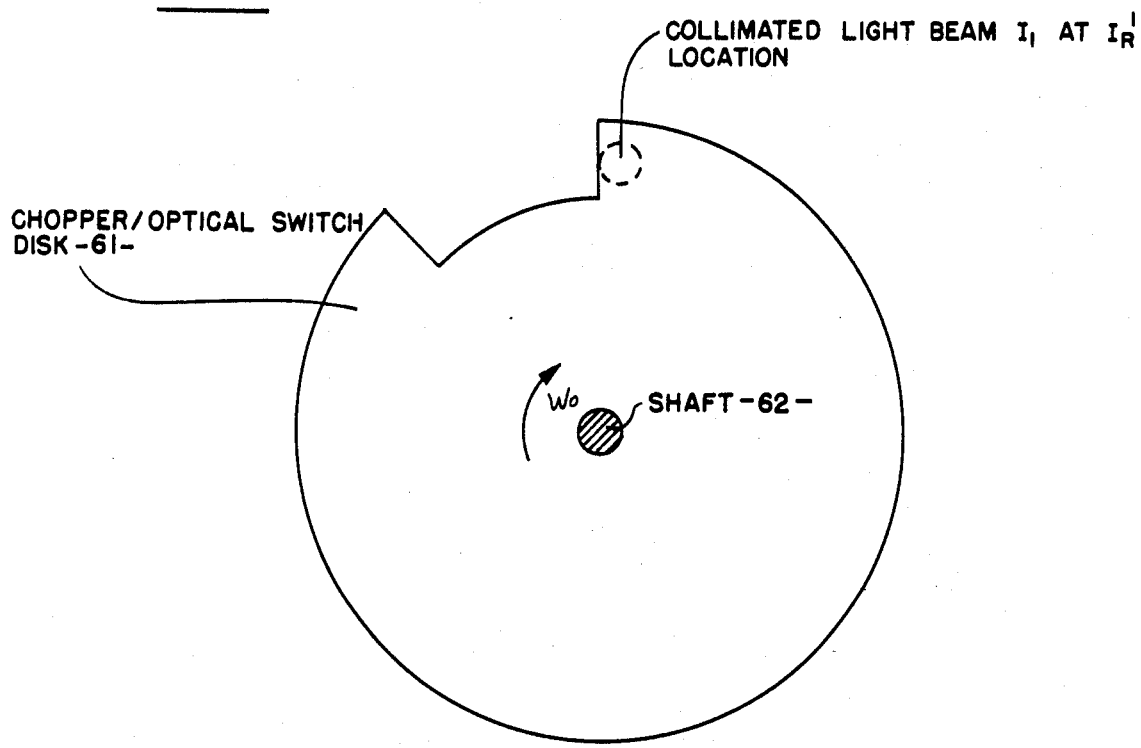
FIG. 11 is a representation of a chopper/optical switching disc for use in the system of FIGS. 8 and 9.

FIG. 10 shows a plan view of an embodiment of mask 34 and shutter 36, which in conjunction with the chopper/optical switch disc 61 shown in FIG. 11, provides a means for easily changing the optical attenuation by 10:1. This is accomplished by designing the light pulse generated by the chopper.optical switch to be sufficiently short in duration so that each shutter opening can be 18°, except for one which is 54°. The diameter of disc 61 in FIG. 11 is not to the same scale as the diameter of mask 34 and shutter 36 in FIG. 10. The ports in the mask are sufficiently small so that there is no partial attenuation of the light pulse passing through the port by the shutter. The one port labeled A is 54° and all others are 18°.

FIG. 10 is the configuration of mask 34 and shutter 36 which exists when there is no attenuation by the shutter. In this representation, the light pulse which passes through the time division attenuator is just starting.

It can be seen however, that if the shutter is displaced at this instant by 18° that all of the ports except the one centered in the 54° shutter segment will be covered throughout the light pulse. Therefore, only one port will be open for each light pulse and the attenuator on an average will pass exactly 1/10 the light it passes when the shutter has a phase change with respect to the light pulse of 18°.

The components of FIGS. 10 and 11 are shown at the time light pulse ($I'_R$) is starting in this condition the shutter 36 does not attenuate the light beam $I_R$ at all. However, shifting shutter 36 stops nine of the ten light beams which pass through mask 34.

The invention provides, therefore, an improved photometric system which uses a time-division optical attenuator to effectuate precise calibration and/or transmittance measurements.

Although particular embodiments of the invention have been shown and described, modifications may be made. It is intended in the claims to cover the modifications which come within the spirit and scope of the invention.

What is claimed is:

1. A photometric system comprising: first means for producing a pulsating light beam; time-division optical attenuator means positioned in the path of the pulsating light beam, and including second means for producing a plurality of like pulsating light beams in response to the pulsating light beam from the first means, and third means adjustable to pass selected ones of the light pulses of the pulsating light beams from the second means to vary the average amount of light passed thereby; a photoelectric detector positioned in the path of the pulsating light beam from the time-division optical attenuator means; and further optical attenuator means positioned in the path of the pulsating light beam between the first means and the photoelectric detector.

2. The photometric system defined in claim 1, in which the pulses passed by said third means of said time-division optical attenuator means are substantially of the same intensity.

3. The photometric system defined in claim 1, in which the adjustable third means in said time-division optical attenuator means varies the average amount of light passed thereby by eliminating a predetermined fraction of the light pulses passing therethrough.

4. The photometric system defined in claim 1, in which said third means in said time-division optical attenuator means is adjustable to maintain the average light intensity reaching said detector within a relatively small range of intensities for different attenuation values of said further optical attenuator means.

5. The photometric system defined in claim 1, in which said first means produces two pulsating light beams consisting of a pulsating reference light beam and a pulsating test light beam, and in which said time-division optical attenuator is positioned in the path of said pulsating test light beam, and in which said further optical attenuator means is positioned in the path of said pulsating test light beam and comprises a test attenuator means; and means for combining the pulsating reference light beam with the pulsating test light beam from said test optical attenuator means and for introducing the resulting combined pulsating light beams to said photoelectric detector.

6. The photometric system defined in claim 5, and which includes reference optical attenuator means positioned in the path of the pulsating reference light beam to establish an average light intensity of the pulsating reference light beam substantially equal to the average light intensity of the pulsating test light beam from the test attenuator means.

7. The photometric system defined in claim 1, in which said further attenuator means comprises a filter to be calibrated.

8. The photometric system defined in claim 1 in which said third means in said time-division optical attenuator means comprises a rotatable shutter positioned in the path of the pulsating light beam and having a predetermined number of ports therein; and means for rotatably driving the shutter in synchronism with the light pulses in the pulsating light beam.

9. The photometric system defined in claim 8, in which the ports of the shutter are adapted to be selectively closed.

10. The photometric system defined in claim 1, in which said second means of said time-division attenuator means comprises a stationary mask positioned in the path of said pulsating light beam and having a predetermined number of ports therein, and said third means of said time-division attenuator means comprises a rotatable shutter positioned coaxially with said mask in the path of the pulsating light beams from said mask and having a corresponding number of ports therein positioned to be aligned with the corresponding ports in said mask, and means for rotatably driving the shutter in synchronism with the light pulses of the pulsating light beam.

11. The photometric system defined in claim 9, in which the ports of the shutter are adapted to be selectively closed.

12. The photometric system defined in claim 1, in which said further attenuator means comprises a plurality of filter devices, and means for selectively positioning the filter devices of said further attenuator means in the light path of the pulsating light beam.

13. The photometric system defined in claim 1, in which said first means produces two pulsating light beams consisting of a pulsating reference light beam and a pulsating test light beam, and in which said time-division optical attenuator is positioned in the path of said pulsating reference light beam, and in which said further optical attenuator is positioned in the path of said pulsating test light beam and comprises a test optical attenuator means; and means for combining the pulsating reference light beam from said time-division optical attenuator with the pulsating test light beam from the test optical attenuator means and for introducing the resulting combined pulsating light beams to said photoelectric detector.

14. The photometric system defined in claim 13, and which includes reference optical attenuator means positioned in the path of the pulsating reference light beam to establish an average light intensity of the pulsating reference light beam substantially equal to the average light intensity of the pulsating test light beam from the test attenuator means.

15. The photometric system defined in claim 13, in which said further optical attenuator means comprises a sample cell.

16. The photometric system defined in claim 1, in which said further optical attenuator means comprises a sample cell.

17. The photometric system defined in claim 1, in which said first means produces two pulsating light beams consisting of a pulsating reference light beam and a pulsating test light beam, and in which said time-division optical attenuator is positioned in the path of said pulsating reference light beam, and in which said further optical attenuator is positioned in the path of said pulsating reference light beam and comprises a reference optical attenuator means; and means for combining the pulsating test light beam with the pulsating reference light beam from the reference optical attenuator means and for introducing the resulting combined pulsating light beams to said photoelectric detector.

18. The photometric system defined in claim 17, and which includes a test optical attenuator means positioned in the path of said pulsating test light beam, said time-division optical attenuator being adjustable to maintain the ratio of the average light intensities in the pulsating reference and test light beams constant within a relatively small range for different attenuation values of the test optical attenuator means.

19. A time-division optical attenuator including: first means for producing a plurality of like pulsating light beams in response to a pulsating light beam incident thereon, and second means adjustable to pass selected ones of the light pulses of the pulsating light beams from the first means to vary the average amount of light passed by the attenuator.

20. The time-division optical attenuator defined in claim 19, in which said second means varies the average amount of light passed by the attenuator by eliminating a predetermined fraction of the light pulses from the beams passing through the first means.

21. The time-division optical attenuator defined in claim 19, in which said second means comprises a rotatable shutter positioned in the path of the pulsating light beams from the first means and having a predetermined number of ports therein; and means for rotatably driving the shutter in synchronism with the light pulses in the incident pulsating light beam.

22. The time-division optical attenuator means defined in claim 21, in which the ports in the shutter are adapted to be selectively closed.

23. The time-division optical attenuator defined in claim 19, in which said first means comprises a stationary mask positioned in the path of the incident pulsating light beam and having a plurality of ports therein, and said second means comprises a rotatable shutter positioned in the path of the pulsating light beams from the first means and having a different plurality of ports therein; and means for rotatably driving the shutter in synchronism with the pulses in the incident pulsating light beam.

24. The time-division optical attenuator means defined in claim 23, in which the ports in the shutter are adapted to be selectively closed.

25. The time-division optical attenuator defined in claim 19, in which a plurality of parallel pulsating light beams are formed and in which selected ones of the light pulses of each of the parallel pulsating light beams are passed.

26. The time-division optical attenuator defined in claim 25, in which the intensity of the parallel pulsating light beams is substantially the same.

27. The time-division optical attenuator means defined in claim 25, and which comprises a stationary mask positioned in the path of the light beam and having a plurality of ports therein for forming the parallel pulsating light beams, and a rotatable shutter positioned in the path of the parallel pulsating light beams from the mask and having a corresponding number of ports therein positioned to be aligned with corresponding ports of said mask; and means for rotatably driving the shutter in synchronism with the light pulses in the pulsating light beams.

* * * * *